United States Patent
Scott (10) Patent No.: US 8,368,412 B2
(45) Date of Patent: Feb. 5, 2013

(54) CORRECTION FOR GAS ENTRAINED WATER ANALYZERS

(75) Inventor: Bentley N. Scott, Garland, TX (US)

(73) Assignee: Phase Dynamics, Inc., Richardson, TX (US)

(*) Notice: Subject to any disclaimer, the term of this patent is extended or adjusted under 35 U.S.C. 154(b) by 374 days.

(21) Appl. No.: 12/804,356

(22) Filed: Jul. 20, 2010

(65) Prior Publication Data

US 2011/0012626 A1 Jan. 20, 2011

Related U.S. Application Data

(60) Provisional application No. 61/271,374, filed on Jul. 20, 2009.

(51) Int. Cl.
*G01R 27/08* (2006.01)
*G01N 27/00* (2006.01)
*G01N 11/00* (2006.01)
*G01F 1/12* (2006.01)

(52) U.S. Cl. ....... 324/694; 73/1.02; 73/53.01; 73/61.41; 702/100

(58) Field of Classification Search .............. 324/694, 324/693, 691, 649, 600, 323, 324, 629, 633, 324/634, 637, 639, 640, 642, 643, 658, 686, 324/689; 73/61.41, 61.43, 61.44, 53.01, 73/1.02, 861.04, 861; 702/1, 25, 24, 45, 702/50, 100, 127
See application file for complete search history.

(56) References Cited

U.S. PATENT DOCUMENTS

| 5,793,216 A | 8/1998 | Constant |
| 6,272,915 B1* | 8/2001 | Kostelnicek et al. ...... 73/152.28 |
| 6,467,358 B1 | 10/2002 | Nishl et al. |
| 2003/0011386 A1* | 1/2003 | Xie et al. ............... 324/694 |
| 2010/0164514 A1* | 7/2010 | Brandt et al. .............. 324/694 |

FOREIGN PATENT DOCUMENTS

EP 0 399 876 A1 11/1990
EP 0 436 286 A2 7/1991

OTHER PUBLICATIONS

Notification of Transmittal of the International Search Report and the Written Opinion of the International Searching Authority, or the Declaration dated Mar. 2, 2011 in connection with International Patent Application No. PCT/US2010/002032.

* cited by examiner

*Primary Examiner* — Hoai-An D Nguyen (57) ABSTRACT

An apparatus for measuring a water content in a multiphase fluid flow stream is provided. The apparatus includes a measurement section configured to obtain a series of electrical measurements of the multiphase fluid flow stream over a first predetermined time interval, and determine a minimum electrical measurement Fmin_baseline from the series of electrical measurements. The measurement section also is configured to calculate a running average of the frequency (Fmin_gas_pattern) from the series of electrical measurements indicative of a change in a gas flow pattern of the multiphase fluid flow stream over a second predetermined time interval. The measurement section further is configured to calculate a corrected electrical measurement F_calc_WC for determining the water content in the multiphase fluid flow stream by subtracting the running average of the frequency. Fmin_gas_pattern from the minimum electrical measurement Fmin_baseline.

21 Claims, 8 Drawing Sheets

| | SALINITY, BY WEIGHT% | | | | | | |
|---|---|---|---|---|---|---|---|
| | 0.10% | 0.50% | 1% | 2% | 3% | 5% | 8% |
| MAXIMUM FREQUENCY, MHz | 222.4 | 213.19 | 210.19 | 205.3 | 201.42 | 195.5 | 189.6 |
| MINIMUM FREQUENCY, MHz | 214.9 | 205.22 | 199.64 | 191.9 | 187.2 | 180.05 | 171.86 |
| MHz SPAN BETWEEN MAXIMUM AND MINIMUM | 7.53 | 7.98 | 10.55 | 13.44 | 14.22 | 15.45 | 17.74 |
| MEAN FREQUENCY | 218.7 | 209.21 | 204.91 | 198.6 | 194.31 | 187.77 | 180.73 |
| SLOPE OF LINES ON FIGURE 2, WC %/MHz | -0.066 | -0.063 | -0.047 | -0.037 | -0.035 | -0.032 | -0.0282 |

CORRECTION FOR GAS ENTRAINED WATER ANALYZERS

CROSS-REFERENCE TO RELATED APPLICATION(S) AND CLAIM OF PRIORITY

The present application is related to U.S. Provisional Patent Application No. 61/271,374, filed Jul. 20, 2009, entitled "CORRECTION FOR GAS ENTRAINED WATER ANALYZERS". Provisional Patent Application No. 61/271,374 is assigned to the assignee of the present application and is hereby incorporated by reference into the present application as if fully set forth herein. The present application hereby claims priority under 35 U.S.C. §119(e) to U.S. Provisional Patent Application No. 61/271,374.

TECHNICAL FIELD OF THE INVENTION

The present application relates generally to measuring the content of one fluid in a multi-fluid mixture and, more specifically, to a method and system for measuring the content of water in crude oil.

BACKGROUND OF THE INVENTION

The chemical and physical characterization of crude, partially refined, and fully refined petroleum products is a common practice in the petroleum industry. Characterizations such as compositional and physical property determinations are used for a variety of purposes. One of their more important uses is when they are done in combination with hydrocarbon well testing to assist in optimizing oil production from a single or series of hydrocarbon wells. Another important use is during the transfer of crude petroleum oil, as occurs during the production, transport, refining, and sale of oil. The accurate determination of water content and validation of the amount of water in crude oil are particularly important during the taxation of crude oil and the sale of crude oil, where the owner or seller of the oil does not want to pay taxes on water and the customer does not want to pay the price of oil for water. For example, crude petroleum oil emerging from production wells can contain large amounts of water, ranging generally from about 1% to as high as 99% water. This value is known as the water cut ("WC").

SUMMARY OF THE INVENTION

A system for determining a water content in a multiphase fluid flow stream is provided. The system comprises an apparatus configured to obtain a series of electrical measurements of the multiphase fluid flow stream over a first predetermined time interval, and determine a minimum electrical measurement Fmin_baseline from the series of electrical measurements. The apparatus also is configured to calculate a running average of the frequency (Fmin_gas_pattern) from the series of electrical measurements indicative of a change in a gas flow pattern of the multiphase fluid flow stream over a second predetermined time interval. The apparatus further is configured to calculate a corrected electrical measurement F_calc_WC for determining the water content in the multiphase fluid flow stream by subtracting the minimum electrical measurement Fmin_gas_pattern from the minimum electrical measurement Fmin_baseline.

A method for determining a water content in a multiphase fluid flow stream using a water content measurement apparatus is provided. The method comprises obtaining a series of electrical measurements of the multiphase fluid flow stream over a first predetermined time interval, and determining a minimum electrical measurement Fmin_baseline from the series of electrical measurements. The method also comprises calculating a running average of the frequency (Fmin_gas_pattern) from the series of electrical measurements indicative of a change in a gas flow pattern of the multiphase fluid flow stream over a second predetermined time interval. The method further comprises calculating a corrected electrical measurement F_calc_WC for determining the water content in the multiphase fluid flow stream by subtracting the minimum electrical measurement Fmin_gas_pattern from the minimum electrical measurement Fmin_baseline.

An apparatus for measuring a water content in a multiphase fluid flow stream is provided. The apparatus comprises a measurement section configured to obtain a series of electrical measurements of the multiphase fluid flow stream over a first predetermined time interval, and determine a minimum electrical measurement Fmin_baseline from the series of electrical measurements. The measurement section also is configured to calculate a running average of the frequency (Fmin_gas_pattern) from the series of electrical measurements indicative of a change in a gas flow pattern of the multiphase fluid flow stream over a second predetermined time interval. The measurement section further is configured to calculate a corrected electrical measurement F_calc_WC for determining the water content in the multiphase fluid flow stream by subtracting the minimum electrical measurement Fmin_gas_pattern from the minimum electrical measurement Fmin_baseline.

BRIEF DESCRIPTION OF THE DRAWINGS

For a more complete understanding of the present disclosure and its advantages, reference is now made to the following description taken in conjunction with the accompanying drawings, in which like reference numerals represent like parts.

DETAILED DESCRIPTION OF THE INVENTION

FIGS. 1 through 8, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged water analyzer system.

During operation of a high water cut oil well, the oil and water mixture can ideally be considered as a dispersion of oil in water wherein the water is the continuous phase and the oil exists as droplets within the continuous water phase. At water cuts above about 80%, the water is usually the continuous phase, and droplets of the oil are dispersed within the water phase. Additionally, a high water cut oil well typically produces oil with a daily average water cut that can shift over several days or weeks of operation. This is especially true as the oil-bearing formation becomes depleted of oil, resulting in higher and higher amounts of water exiting from the well. However, an oil well is not an ideal system, and its compositional behavior can be quite dynamic and random over a period of time as short as several seconds or minutes. For example, water flooding (e.g., water injection from above the ground down into the subterranean oil-bearing formations) can be used to push and carry oil up to the surface of the Earth. At any given moment, more or less water can enter the oil well drill string. This can cause variation in the amount of water in the flow stream exiting from the well. Additionally, as the oil and water mixture travels up the drill string (which can be as long as a mile or more), oil droplets can coalesce into larger collections, or "slugs", of oil. A slug of oil can be considered to be a high concentration of oil with a reduced level of entrained water. Such coalescence of oil then can cause variation in the amount of water exiting a well at any given moment. During operation of a well experiencing oil coalescence, slugs of oil with reduced amounts of water and slugs of water with reduced amounts of dispersed oil can exit from the well. Thus, a water content determination system in contact with the discharge of such a well will be measuring the water content of such slugs.

Water content determinations and validations can be conducted on-line and off-line during petroleum processing. On-line determinations include instruments such as densitometers, capacitance probes, radio frequency probes, and electromagnetic characterization systems, including those which are referred to, for historical reasons, as "microwave analyzers".

Salinity in the water associated with crude oil presents a further challenge to such water cut determination systems and methods because salinity has a significant effect on the electromagnetic properties of the oil and water mixture. Additionally, the amount of salinity in the water can vary, even from the same well. For example, water percolation within subterranean oil-bearing formations can change course over time resulting in changing amounts of dissolved salts in the water. One method of correcting for the effects of salinity changes is for an operator to manually measure the salinity of the water phase and input the measurement into the analyzer to allow the analyzer to select pre-established offset correction factors based on the inputted salinity and test-generated calibration curves. A manual determination of salinity is commonly made using a refractometer to measure the refractive index of the water phase. This index is then correlated to a percent salinity using a pre-established relationship between percent salinity and refractive index. The percent salinity is then entered into the analyzer as previously described. The pre-established relationship between a percent salinity and a refractive index can be developed by measuring the refractive index of a series of standardized saline solutions to establish a data reference set, and equations can be fitted to the data set.

Sometimes, the refractive index of the aqueous phase cannot be easily determined. For example, the aqueous phase may be so turbid as to prevent an accurate reading from being obtained. Or, in the case of an emulsified oil-water system, the refractive index cannot be read unless the system is somehow de-emulsified and allowed to separate into a clear-enough aqueous phase to allow a refractive index to be determined.

Such refractive index measurement techniques or other separate salinity measurement techniques are, thus, inherently unreliable in systems that are susceptible to emulsification and require additional apparatus, further complicating the total measurement system.

Figure 1:
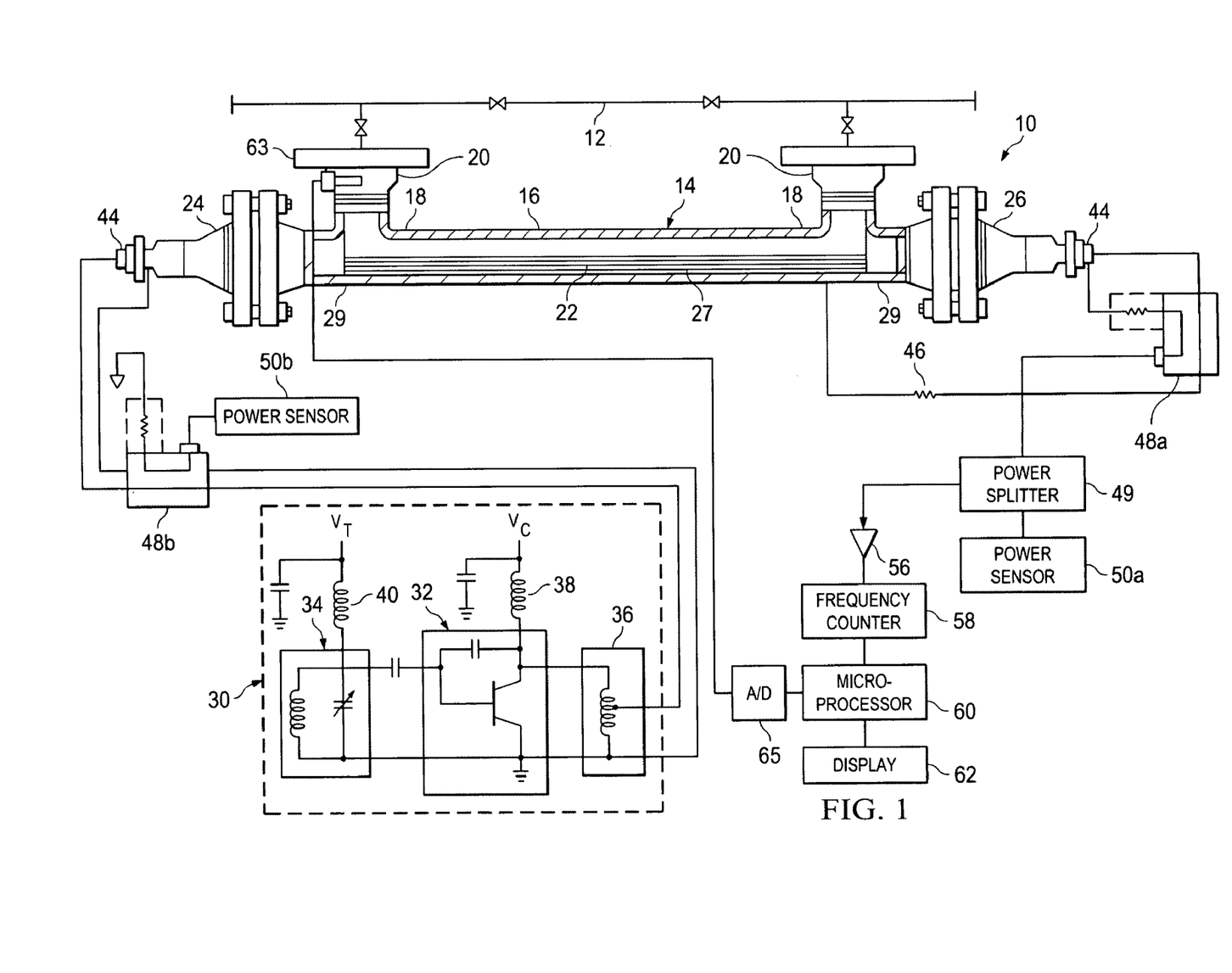
FIG. 1 illustrates an apparatus for measuring one fluid in a multi-fluid mixture according to an embodiment of this disclosure.

FIG. 1 illustrates an apparatus 10 for measuring one fluid in a multi-fluid mixture according to an embodiment of this disclosure. The embodiment of the apparatus 10 illustrated in FIG. 1 is for illustration only. Other embodiments of the apparatus 10 could be used without departing from the scope of this disclosure.

FIG. 1 shows a diagram of an apparatus 10 for measuring the concentration of one substance or material, such as water, in another substance or material, such as crude petroleum oil, that is being transmitted as a liquid mixture flow stream through a pipeline. The apparatus 10 is particularly adapted for interconnection with a fluid transmission pipeline 12 for sampling the pipeline flow stream. Alternatively, the apparatus 10 might become part of the pipeline. The apparatus 10 includes a fluid flow conducting and a measurement section 14 comprising an outer conduit section 16, including spaced apart pipe tee sections 18 having conventional flange portions 20 formed thereon for connection to branch conduit portions of the pipeline 12. The measurement section 14 comprises a coaxial transmission line that includes a center conductor 22 preferably formed of a metal such as stainless steel that extends between opposed end support parts 24 and 26. In particular embodiments, the center conductor 22 preferably comprises a generally cylindrical rod or tube member coaxially arranged in the conduit section 16 and provided with an outer sheath 27 formed of a material having a relatively low dielectric loss tangent, preferably less than 0.1 at a frequency of 1.0 GHz. The outer sheath 27 preferably comprises a relatively easy-to-fabricate plastic such as polypropylene, a plastic sold under the trademark Delrin or one of the fluorocarbon plastics. Alternatively, certain ceramics or other materials may also be used as the outer sheath 27 as long as they are low loss tangent dielectric materials. In particular embodiments, the fit between the outer sheath 27 and the center conductor 22 is preferably a forced or line-to-line fit although some clearance may be permitted as long as fluid flow between the center conductor 22 and the outer sheath 27 is prohibited. In an apparatus where the center conductor 22 has a diameter of 0.25 inches, the outer diameter of the outer sheath 27 is preferably at least about 0.50 inches or, alternatively, a ratio of the outer diameter of the outer sheath 27 to the outer diameter of the center conductor 22 is in the range of about two to one.

It has been determined that with the provision of an outer sheath 27 formed of one of the above-mentioned materials and in the proportions described, that the electrical circuit for propagating microwave radiation through the apparatus 10 retains a high quality signal resolution characteristic in liquid mixtures of oil and water (for example, wherein the water content is relatively high, that is on the order of more than 5% to 10% by volume). With this type of center conductor arrangement, the circuit associated with the apparatus 10 and described herein below retains good field intensity or prevents short circuiting of the center conductor 22 to the outer conductor in an unwanted location, the oscillator circuit retains its good load-pulling characteristics with good resolution of phase, and the interface between the outer sheath 27 and the fluid in the conduit section 16 is a new propagation medium that has desirable operating characteristics.

When the apparatus 10 is operating with a liquid composition that is high in water content or a so-called water continuous phase, the conductivity of the composition is high compared to a good dielectric but low compared to a good conductor, and, of course, the liquid composition is in direct contact with the wall surfaces of the measurement section 14 including the center conductor 22. The outer sheath 27 prevents the radio frequency (RF) energy (e.g., microwave energy) from being shorted out immediately at the point where the RF energy enters the measurement section 14 or where the fluid cross section begins. Moreover, the outer sheath 27 now becomes the primary region where the RF field is propagated with the conductive fluid becoming a pseudo outer wall of the measurement section 14 in place of the wall of the conduit section 16. The cross sectional measurement of the water-in-oil composition is still preserved due to the large skin depth of the microwave or RF energy at the operating frequency. This skin depth is large through the water as the conducting medium of the outer half of the coaxial transmission line formed by the measurement section 14. The dielectric structure is now the outer sheath 27. The properties of the propagated RF energy still reflect the changing content of the oil in the water, and this is related through pulling of the unisolated oscillator that is described herein below. The outer sheath 27 is thick enough to maintain a reasonable coaxial impedance to be able to propagate the RF energy into the measurement section 14 and maintain a measurement capability. A very thin dielectric coating on the center conductor 22 will cause very low impedance with a liquid composition having a high water content, and, therefore, the RF energy would be reflected at the fluid interface.

RF energy is not propagated in the interior of a good conductor. The conductor guides the electromagnetic waves. The energy travels in the region between the conductors in a coaxial transmission system with a good dielectric. The currents that are established at the conductor surfaces propagate into the conductor in a direction perpendicular to the direction of the current density. The current density or electric field intensity established at the surface of a good conductor decays rapidly looking into the conductor. When the conductor is resistive or low conductivity, this depth into the conductor increases rapidly. This phenomenon is known as skin depth.

As shown in FIG. 1, the center conductor 22 extends through opposed end block members 29 that are also preferably formed of a relatively high insulative material such as a fluorocarbon plastic.

The measurement section 14 is operably connected to a source of radio frequency (RF) or so-called microwave energy comprising an unbuffered or unisolated, free-running oscillator 30. The oscillator 30 includes an active circuit 32 operably connected to a tuning circuit 34 and to an impedance matching network circuit 36. The active circuit 32 is adapted to receive a constant DC voltage, Vc, from a source not shown and by way of a filter circuit 38. The tuning circuit 34 also is adapted to receive a controllable DC voltage, Vt, from another source, not shown, by way of a second filter circuit 40. The oscillator 30 has an appreciable load-pulling characteristic. The fundamental operating frequency of the oscillator 30 is changed as the complex load is changed on the output circuit of the oscillator 30. The oscillator 30 is preferably of a type commercially available such as from Avantek Company, Santa Clara, Calif. as their model VTO 8030 voltage controlled oscillator. In a particular embodiment, the oscillator 30 has a maximum load-pulling characteristic of about 35 MHz at a nominal 200 MHz operating frequency into all phases of a short circuit at the end of a 50 Ohm line stretcher (approximately 0.5 dB return loss). The oscillator 30 is operably connected to the measurement section 14 through a suitable connector 44 that is in electrically conductive engagement with the center conductor 22 at the end support part 24 and at the opposite end of the center conductor 22 through a second connector 44, a resistance 46 and with the conduit section 16 as illustrated. The end support part 26 is also adapted to connect the center conductor 22 with a 10 dB directional coupler 48a that is operable to sample the microwave energy or power transmitted through the coaxial measurement section 14. The directional coupler 48a is connected to a power splitter 49 which is connected to a power sensor 50a. The directional coupler 48a may be of a type manufactured by Minicircuits Company of Brooklyn, N.Y. as their model ZED-15-2B. The power splitter 49 may be of a type ZFSC-2-2 also manufactured by Minicircuits. The power sensor 50a may be of a type 437B manufactured by Hewlett Packard of Sunnyvale, Calif.

A second directional coupler 48b is interposed in the circuit between the end support part 24 and the oscillator 30 and is connected to a second power sensor 50b. The directional couplers 48a and 48b may be of identical configuration. The directional coupler 48a is connected to the power splitter 49 which provides an output signal that is amplified by an amplifier 56. The output of the amplifier 56 is adapted to be input to a frequency counter 58 which is also adapted to be connected to a microprocessor 60. A suitable digital display or readout device 62 is connected to the microprocessor 60. The amplifier 56 may be of a type commercially available from the above-mentioned Minicircuits Company as their model ZFL-500. The frequency counter 58 may be of a type manufactured by Hewlett Packard Company as their model 5342A, and the microprocessor 60 may be of a Hewlett Packard type 9836. In a particular embodiment, the apparatus 10 includes a temperature compensation circuit including a thermocouple 63 operably connected to a conversion circuit 65 to provide a suitable digital signal to the microprocessor 60.

In operation, the changing dielectric constant presented by the material flowing through the measurement section 14, such as caused by the presence in a liquid mixture, for example, of varying amounts of water in oil or oil in water, causes the oscillator 30 to change its operating frequency over a relatively narrow frequency band as compared with the nominal operating frequency of the oscillator 30. For example, the oscillator 30, in a particular, can be pulled from its nominal operating frequency through a range of about 20 MHz by the changing dielectric constant of the medium flowing through the measurement section 14.

Figure 2:
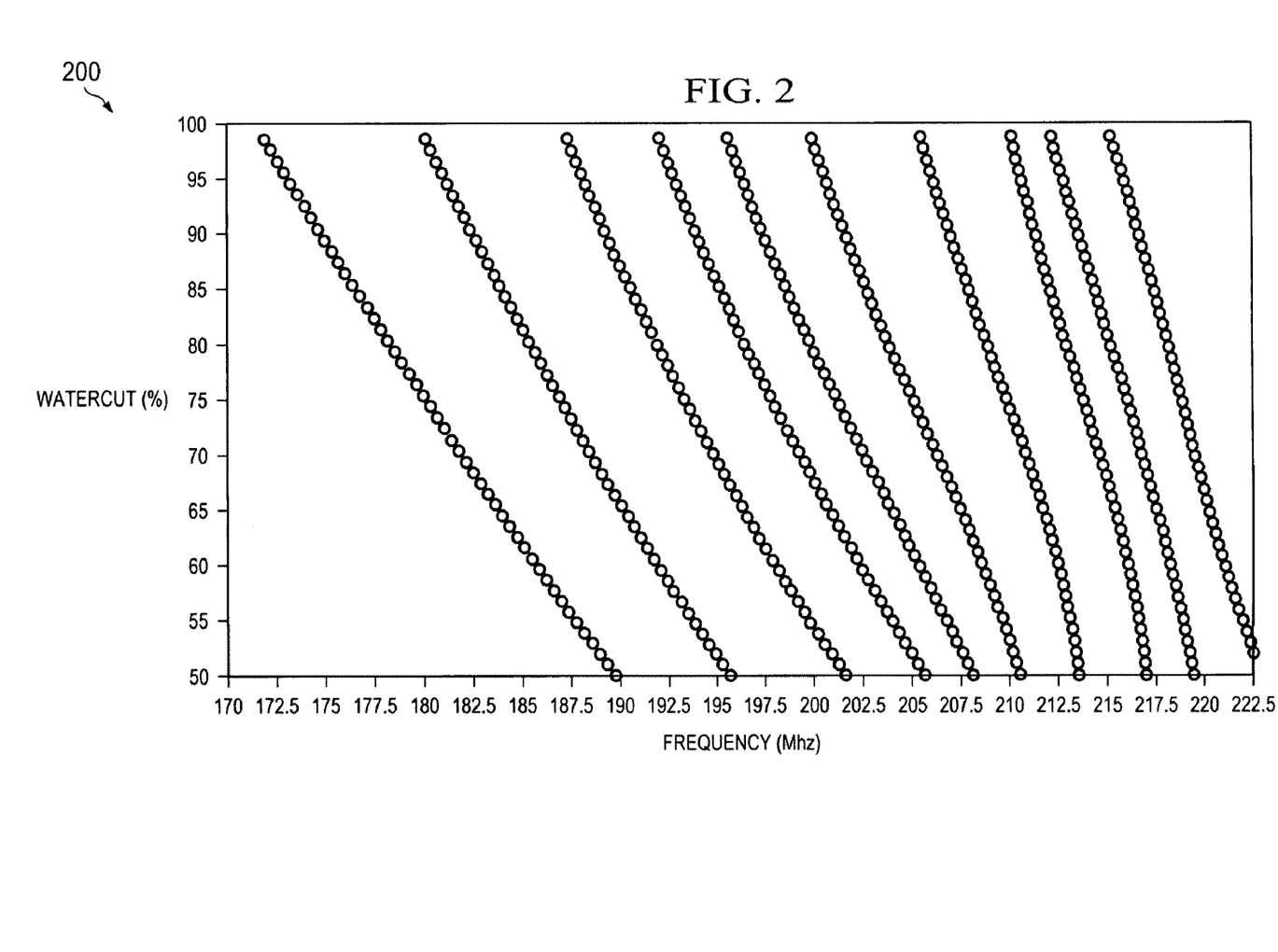
FIG. 2 shows a graph of a family of water cut versus permittivity frequency calibration curves for different salinities of a water phase according to an embodiment of this disclosure.

FIG. 2 shows a graph 200 of a family of water cut versus permittivity frequency calibration curves for different salinities of a water phase according to an embodiment of this disclosure.

As shown in FIG. 2, calibration curves were assembled to relate the electromagnetic (e.g., electrical) properties for water-continuous dispersions of oil to the water content of such mixtures. Specifically, curves relating salinity, water cut, and microwave permittivity frequency in MHz (f) were constructed using a high water cut measurement system. For the frequency curves, water cut percentages ranged from 50% to 100% and were tested at salinities including 0.1%, 0.2%, 0.3%, 0.5%, 1.0%, 1.5%, 2.0%, 3.0%, 5.0%, and 8.0%. FIG. 2 shows the resulting family of curves. Note that an equation can be fitted to the family of curves.

Figure 3:
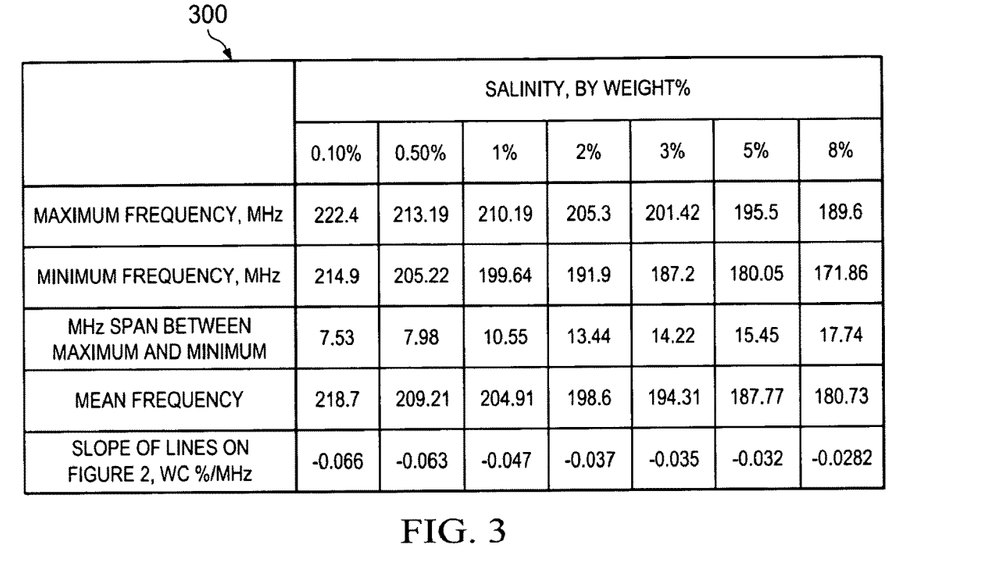
FIG. 3 shows a table of data illustrating key aspects of the graph in FIG. 2 according to an embodiment of this disclosure.

FIG. 3 shows a table 300 of data illustrating key aspects of the graph 200 in FIG. 2 according to an embodiment of this disclosure.

As shown in FIG. 3, the table 300 of data shows the minimum, mean, and maximum frequencies for the family of curves in graph 200. The spans between the minimum and maximum frequencies, and the slopes of the lines on graph 200 also are detailed. Note that the minimum frequency also corresponds to 100% WC or zero oil content. Thus, the minimum is the permittivity frequency of the pure saline water phase. Note that an equation or equations also can be fitted to the data and values in FIG. 3.

Figure 4A:
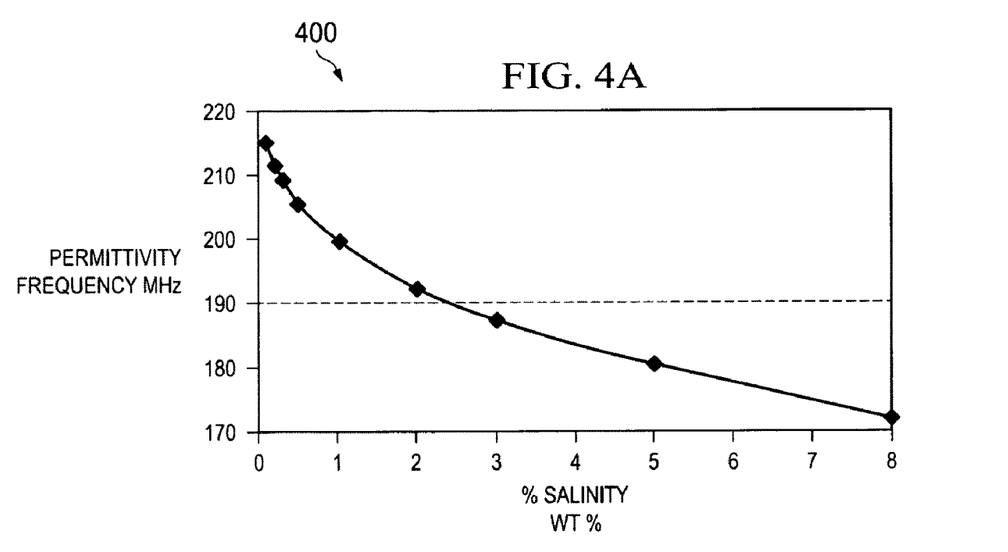
FIG. 4A shows a graph relating permittivity frequency to salinity for an aqueous phase with zero oil content according to an embodiment of this disclosure.

FIG. 4A shows a graph 400 relating permittivity frequency to salinity for an aqueous phase with zero oil content according to an embodiment of this disclosure.

As shown in FIG. 4A, graph 400 illustrates the relationship between permittivity frequency and salinity for the saline water phase at 100% WC or zero oil content. Note that an equation can be fitted to the data in FIG. 4A.

Figure 4B:
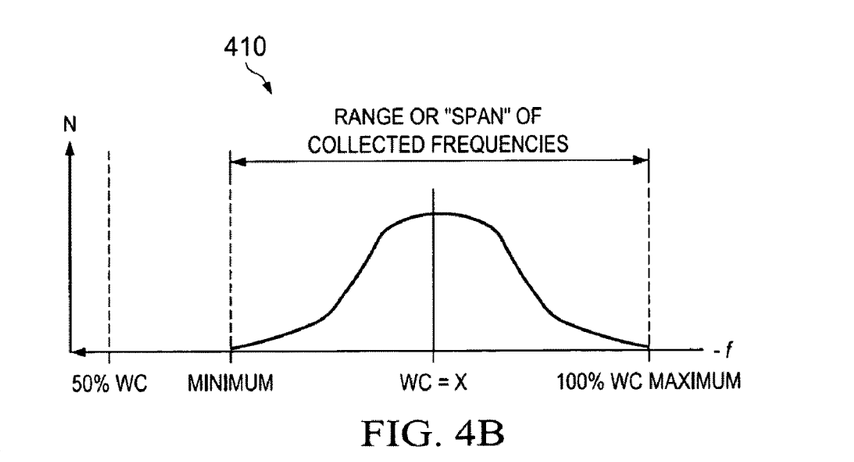
FIGS. 4B, 4C, and 4D show histograms of electrical property readings and waters of a high water cut crude petroleum oil emerging from an oil production well according to an embodiment of this disclosure.
Figure 4C:
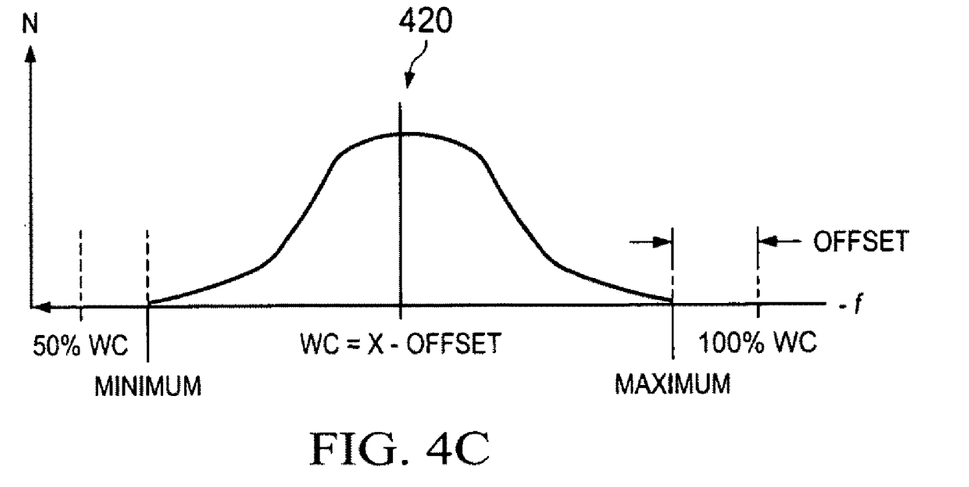
Figure 4D:
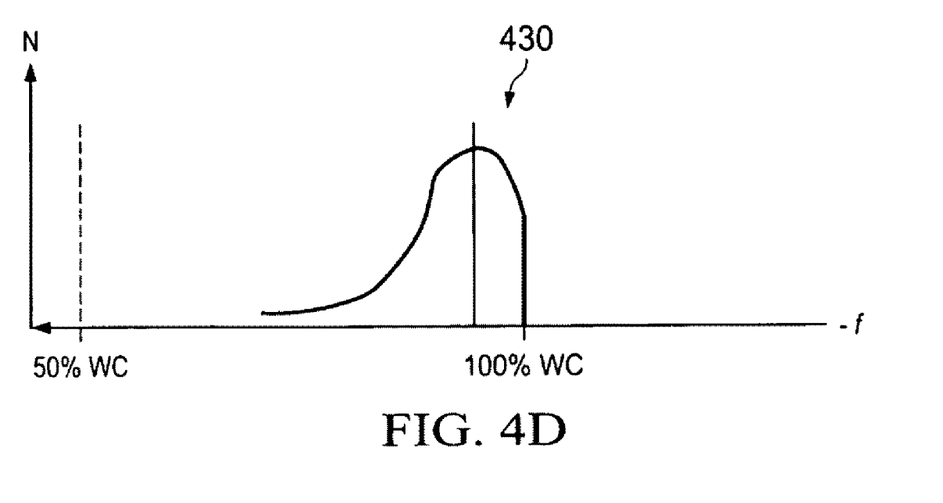

FIGS. 4B, 4C, and 4D show histograms of electrical property readings and waters of a high water cut crude petroleum oil emerging from an oil production well according to an embodiment of this disclosure.

With regard to FIGS. 4B through 4D, a series of graphs show hypothetical histograms of frequency measurements taken by an electromagnetic characterization system directly in contact with a flow stream from a high water cut oil well. In these histograms, the flow stream is assumed to always be water-continuous, and the salinity is assumed to be constant over the length of the collection of the readings. The vertical axis of each histogram depicts the number of readings whereas the horizontal axis depicts the frequency of a particular reading. In this case, since salinity is assumed to be constant, the horizontal axis can also be considered to represent the water content of the flow stream. Thus, the histograms also depict the distribution of the hypothetical water cuts from a high water cut oil well.

FIG. 4B shows a histogram 410 with a normal distribution of frequencies (e.g., water cuts). In this instance, the average water cut is shown as "X", and the minimum and maximum are also shown. Because the water content cannot exceed 100%, the right tail of the distribution stops at 100% water cut. Note that the range or "span" of the water cuts also is shown stretching from the minimum to the maximum of the distribution.

FIG. 4C shows a similar histogram 420, but in this instance, the average water cut is shown as "X minus offset" where the maximum water content encountered in the readings is 100% minus the offset.

FIG. 4D shows a histogram 430 depicting a non-normal distribution of readings wherein the average water content is high enough and close enough to 100% such that the right half of the distribution is truncated.

In actual operation of a high water cut oil well, it has been found that most wells produce some output that is substantially 100% water for short periods of times. Such would be the case as shown in FIGS. 4B and 4D. In those instances, the minimum frequency encountered represents the frequency of the aqueous phase. By utilizing the graph 400 of FIG. 4A (or an equation fitted to the graph), the salinity of the well output can thus be determined. Once the salinity is determined, the water cut measurements from an electromagnetic characterization system, such as a microwave water cut analyzer, can be corrected for the change in the salinity from a previously inputted salinity. A problem with utilizing this approach is knowing when enough readings have been gathered to then select the minimum frequency as the frequency of the aqueous phase. If the distribution is as shown in FIG. 4D, the truncated shape can indicate that a substantially pure water phase has been read a multiple of times. Thus, one can rely on the minimum frequency as substantially equal to the frequency of the aqueous phase (e.g., 100% WC) if the output of the well is not emulsified. However, if the distribution is normal and the output of the well is non-emulsified, then the "length" of the tails of the distribution will tend to "grow" over time as more readings are collected on the random variations of water content in the flow stream exiting from the well.

FIG. 4A shows the span in MHz of frequency, at different salinities, between the minimum and maximum frequency corresponding to water cuts of 100% and 50%, respectively. If the typical salinity and range of water cuts are known for a given well, then a span of typical frequencies can be determined. For example, if a given well swings between 50% and 100% WC at 2% salinity then the characteristic span of frequencies is 13.44 MHz. Thus, a span of 13.44 MHz can be used to test when enough readings have been collected such that the minimum frequency corresponds to the pure aqueous phase at 2% salinity. However, the salinity of the well can change over time, either upwards or downwards. If the salinity shifts downwards, for example, to 1.9%, then the span of 13.44 MHz would never be achieved unless the well swings through a range of water contents wider than 50% to 100%. To that point, a slightly reduced span can be applied to account for the downward shift in salinity. Thus, a Heuristic Salinity™ can be derived.

In measuring the content of water in crude oil, it has been considered necessary with conventional systems to first perform a separation process to remove as much gas from the mixture as possible before subjecting the mixture to a microwave measurement technique. This added gas separation process at each well or elsewhere in the fluid gathering system is, of course, expensive and requires facilities that must be continuously maintained. At times, these physical separators become too small for the increased production rates and incomplete separation or foaming is seen at the output of the liquid portion of the separator.

Therefore, it is highly desirable to be able to measure the amount of water in a crude oil flowstream at the wellhead or before significant separation processes are required, particularly in multi-owner oil fields where production is commingled before separation is performed. There are, of course, other applications wherein it is desirable to know the content of one fluid in a multi-fluid mixture.

Water analyzers using permittivity are affected by entrained gas bubbles from incomplete separation. Therefore, methods to reduce the gas effect are important for correct water percentage measurement. In $CO_2$ floods, both gas breakout and entrainment create difficult separation problems in both conventional and cyclone separators.

Gas is a random effect. If the bubble sizes are small and uniformly distributed due to mixing and attempts at separation such as after a cyclone separator, then the effects can be seen as short term rapid changes in the parameters of measurement. Oil and water are also uniformly distributed due to the mixing effects of a cyclone system or the like, but these changes versus time will be less rapid and more uniform due to the effects of gravity in the well string. Gravity acts like a separator in the Earth allowing water and oil to accumulate in patterns.

There are two variables in the gas to be considered. One is the gas quantity, and the other is a pattern of the quantity changing due to the characteristics of the piping and well string height. In a $CO_2$ flood, it is possible that a lot of the entrained gas may be due to flash after the well choke, and this process may produce more consistent bubble size and quantity over standard production methods such as gas lift wells. There will be two effects on the data average: the first being short-term effects due to the changing gas content and the second being long-term effects due to the pipe string length, heights of piping and other factors affecting a pattern of gas quantity.

Calculations using moving averages versus time appear to be effective in removing the effects of gas effects in measurements if both short-term and long-term effects are considered. In the case where measurement is by load pull, the minimum frequency versus time establishes the maximum water percentage and the equivalent salinity for that well in the manner described using Heuristic Salinity™. In the case of using moving averages as described in this disclosure, the minimum frequency period should be respective of the short term period of changing gas fraction. Since separators and wells will at some point in time produce 100% water when the well is water continuous and very high in water content, this minimum frequency can be used as a baseline frequency if there is no gas present. This new baseline frequency is a long term time interval to establish the 100% water case including the effect that uniformly distributed gas has on the overall salinity, and this will provide a frequency minimum. Other microwave methods have comparable parameters that can be used to establish the 100% water point similar to that just described for load pull systems, but these other microwave methods cannot handle gas entrainment. The minimum frequency (maximum water) point is established versus a long term time interval (for example, 15 minutes), and this minimum frequency is used as the baseline frequency (Fmin_baseline) to establish Heuristic Salinity™ when there is no gas present. With gas, this time interval is dependent upon flow rates which affect the amount of uniform gas seen in the liquids and changing water percentage.

In a typical load pulled system, the instantaneous frequency is used to determine the Heuristic Salinity™ and the water percentage. The problem with having entrained gas is that gas changes the apparent Heuristic Salinity™ calculated due to the noisy background gas that gives the impression of a reduced salinity (or actually conductivity of the cross section being measured). If the gas is constant, the consistency alleviates the effect of the gas, and the Heuristic Salinity™ routine will correct for its presence. If the gas content changes, the fluctuations cause the Heuristic Salinity™ to change quickly with time only if the Heuristic Salinity™ is allowed to change quickly within the software routine. The problem is to determine how and when the Heuristic Salinity™ needs to be re-established, or the constant correction will always give improper results. These effects have been seen in real field cases where expected constant gas versus changing gas was present.

In embodiments of this disclosure, the Heuristic Salinity™ is calculated as previously described except that the selection of the minimum frequency is replaced by a frequency resulting from a calculation taking into account the short term gas effects which move the salinity baseline frequency (baseline frequency or Fmin_baseline), gas bubble sort term average (F_average) and gas pattern (Fmin_gas_pattern) changes.

In particular embodiments, the proper selection of time intervals for the baseline frequency (Fmin_baseline), short term gas effects (F_average) and gas pattern (Fmin_gas_pattern) are derived from data taken in real time at the site and can be changed in the field or analyzed and changed later to achieve proper correction.

Figure 5:
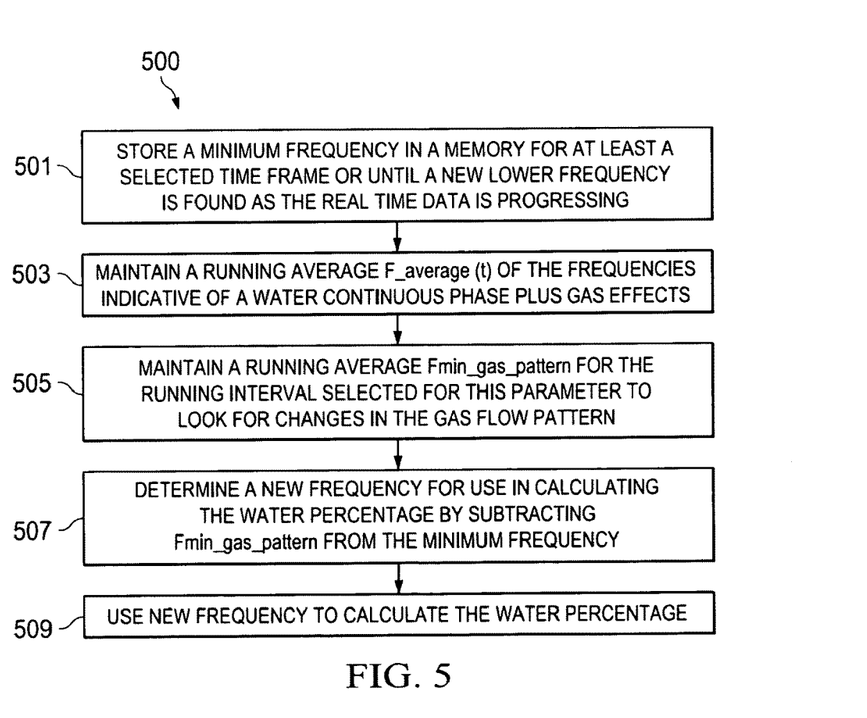
FIG. 5 illustrates a method of operating an analyzer system according to an embodiment of this disclosure.

FIG. 5 illustrates a method 500 of operating an analyzer system according to an embodiment of this disclosure.

In one embodiment of this disclosure, an analyzer system, such as apparatus 10, performs method 500.

As shown in FIG. 5, a minimum frequency (Fmin_baseline) is stored in a memory for at least a selected time interval or until a new lower frequency is found as the real time data is progressing (block 501). In particular embodiments, this value is selected by looking at the noise in the data that should represent the bubble pattern changes versus time. This bubble pattern remains reasonably consistent until something changes in the process causing the bubble pattern to be altered. It is this F_min_baseline which sets the variable inside of the Heuristic Salinity™ routine that sets where 100% water occurs. The gas changes F_min_baseline because the gas alters the cross sectional resistivity (conductivity) of the salt water at 100% water (plus gas). For example, if a time interval of 15 minutes is selected for the Fmin_baseline determination, then the analyzer system stores the minimum frequency in memory for at least the time interval of 15 minutes or until a new lower frequency is found as the real time data is progressing. In cases of dynamically changing gas, this time interval is shorter. Although 15 minutes is used as an example of a time interval in this embodiment, one of ordinary skill in the art would recognize that a shorter or longer time interval could be utilized without departing from the scope or spirit of this disclosure.

A short term running average of the frequencies is maintained (block 503). This short term running average (not a minimum frequency) is representative of the average frequency plus gas more or less in the form of bubbles instead of slugs or large pockets. This time interval could be equal to the above Fmin_baseline time interval or longer. An average of the frequencies is seen as a short term running average from time=NOW backwards in time until time=INTERVAL. For example, in one embodiment, the short term running average INTERVAL of time is set to equal 1 minute with a measurement interval (time between analyzer readings read by the analyzer system) of 10 seconds. In such an embodiment, the frequency F_sum (60 seconds) is the sum of the 6 data points of frequency, and the average of the first 6 data points is calculated as shown in Equation 1 below:

$$F\_average(60\ seconds) = F\_sum(60\ seconds)/6. \quad [\text{Eqn. 1}]$$

At time=60+10 seconds, the new average is calculated as shown in Equation 2 below:

$$F\_average(60+10) = F\_sum(10\ sec\ to\ 60\ sec)/6. \quad [\text{Eqn. 2}]$$

Accordingly, a new average is calculated as shown in Equation 3 below:

$$F\_average(t) = F\_sum((t-60)\ sec\ to\ t\ sec)/6. \quad [\text{Eqn. 3}]$$

Although 1 minute is used as an example of an INTERVAL of time and 10 seconds is used as a measurement interval in this embodiment, one of ordinary skill in the art would recognize that a shorter or longer INTERVAL of time and measurement interval could be utilized without departing from the scope or spirit of this disclosure.

A second running average of the frequency (Fmin_gas_pattern) also is maintained for the running interval selected for this parameter to look at changes in the gas flow pattern (block 505). This second running average takes into consider slugs of gas and larger voids created by gas over the entrained bubbles. For example, in one embodiment, the running interval for the second running average is set to 4 minutes. The goal is to look for the minimum frequency during this interval that may represent the all water case plus the gas effects. The running interval for the second Fmin_gas_pattern is calculated in a similar fashion to the running interval for the average of the frequencies. Although 4 minutes is used as an example of a running time interval in this embodiment, one of ordinary skill in the art would recognize that a shorter or longer running time interval could be utilized without departing from the scope or spirit of this disclosure.

A new frequency for use in calculating the water percentage is determined (block 507). This frequency F_calc_WC represents the resulting average frequency using a salinity selected that compensates for the gas affecting the apparent salinity of the water and the gas bubbles minus the slugs of gas. At each measurement interval (for example, 10 seconds), the new frequency F_calc_WC for use in calculating the water percentage is calculated as shown in Equation 4 below:

$$F\_calc\_WC = F\text{min\_baseline} + (F\_average(t) - F\text{min\_gas\_pattern}). \quad [\text{Eqn 4.}]$$

This new frequency is then used in the normal routines for load pulled oscillator water analyzer systems to calculate the water percentage (block 509). The Heuristic Salinity™ was derived earlier with the Fmin_baseline. The subtraction of the Fmin_gas_pattern returns the baseline to the one established by Fmin_baseline due to gas pattern effects. In addition, this subtraction provides some compensation for the fact that the water percentage used in the oilfield is defined as the portion of the liquid phase which does not include the gas occlusions. The subtraction can be modified by multiplying or dividing one or the other values to better represent the actual conditions in the field.

In a particular embodiment, the first predetermined time interval and the second predetermined time interval are selected using one or more probability density functions.

These same techniques can be used for reducing the noise effects of the density from a measurement within a Coriolis meter and, therefore, may provide better density and flow measurement under the influence of gas. This is because the mass flow measured by the Coriolis meter is divided by the density. Therefore, if the density is more stable, the conversion should be better.

Although the above embodiments are described in relation to systems that use microwave analyzers to determine the water content of a multiphase fluid, one of ordinary skill in the art would recognize that one or more aspects of the embodiments of this disclosure also can be used in conjunction with other analyzer systems, such as optical systems.

Figure 6:
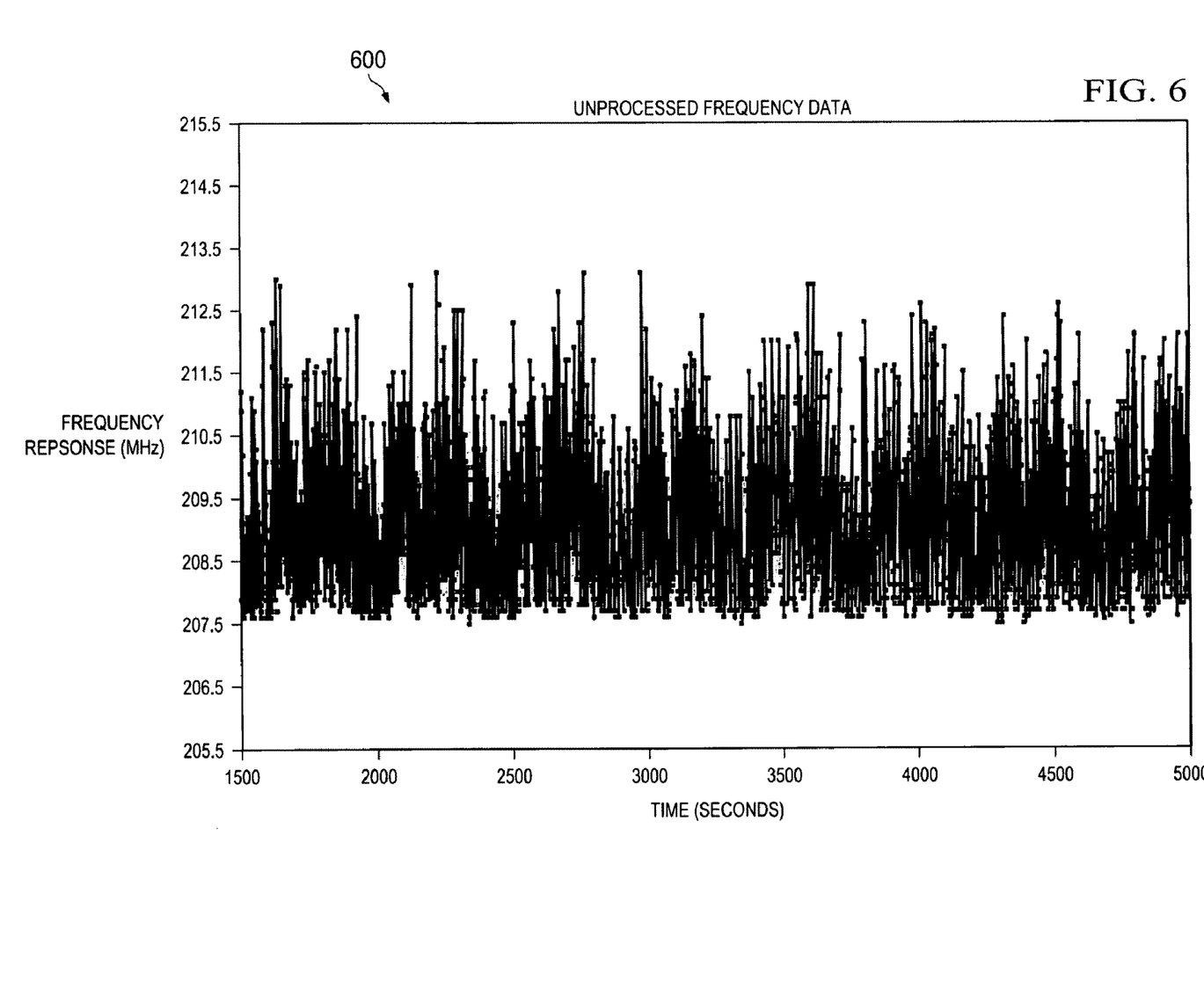
FIG. 6 illustrates a graph of unprocessed frequency data according to an embodiment of this disclosure.

FIG. 6 illustrates a graph 600 of unprocessed frequency data according to an embodiment of this disclosure.

In this embodiment, the frequency data was taken every 10 seconds. The calculated water percentage from this data shows a range from 40% to 100% due to the gas.

Figure 7:
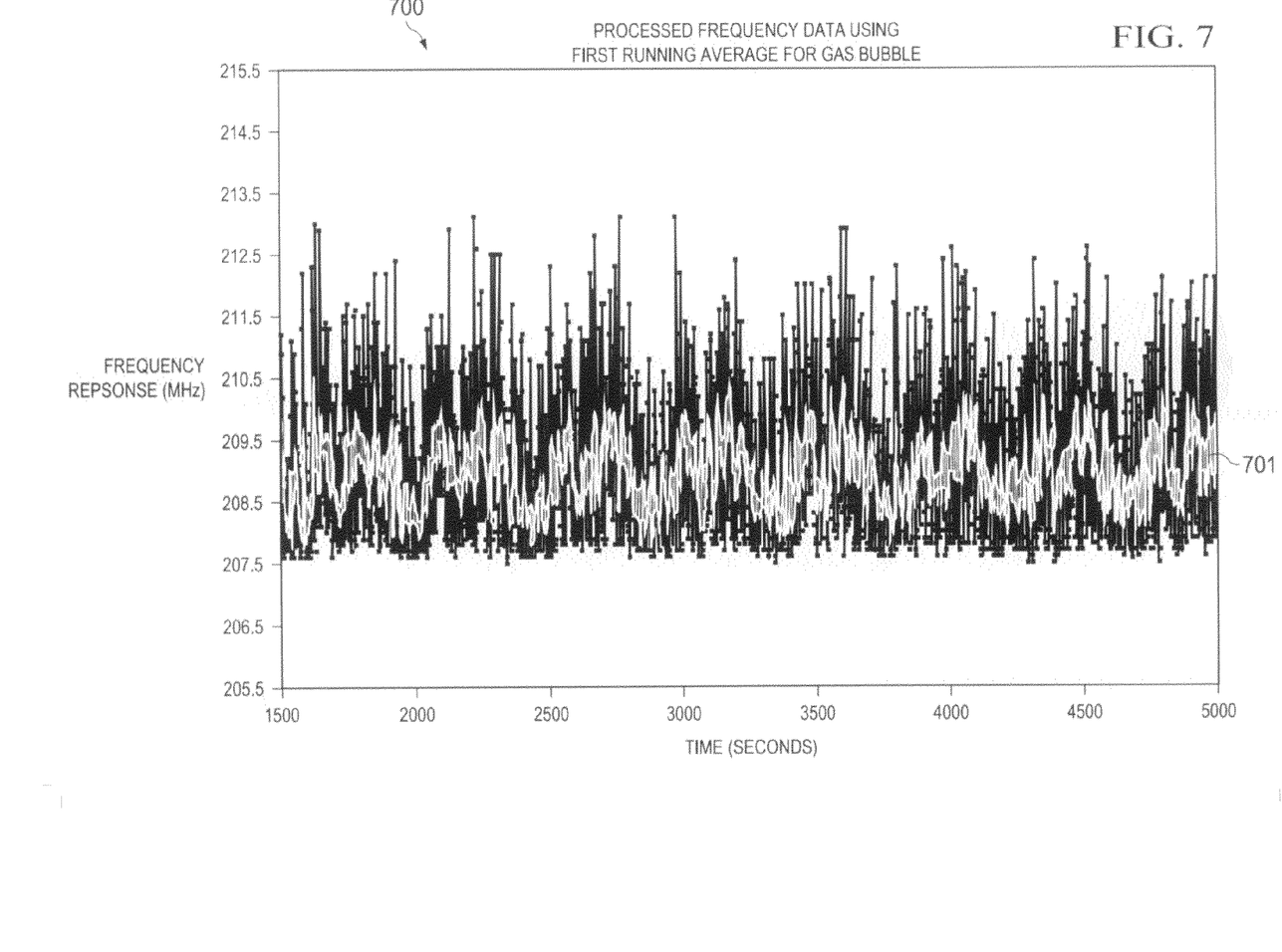
FIG. 7 illustrates a graph of frequency data filtered by a first filter using a 6-samples (1 minute) running average according to an embodiment of this disclosure.

FIG. 7 illustrates a graph 700 of frequency data filtered by a first filter using a 6-samples (1 minute) running average according to an embodiment of this disclosure.

Graph 700 illustrates the original frequency data and a first filter using a 6-samples (1 minute) running average. The white area 701 within the frequency data indicates the filtered data. Although the data shows that this first filter reduces the swing considerably, there remains an offset from the minimum frequency due to what is thought to be gas flow patterns where gas pockets exists in various sizes versus time creating an increasing baseline offset. Accordingly, the longer term more graceful changes are due to changing water percentage.

Figure 8:
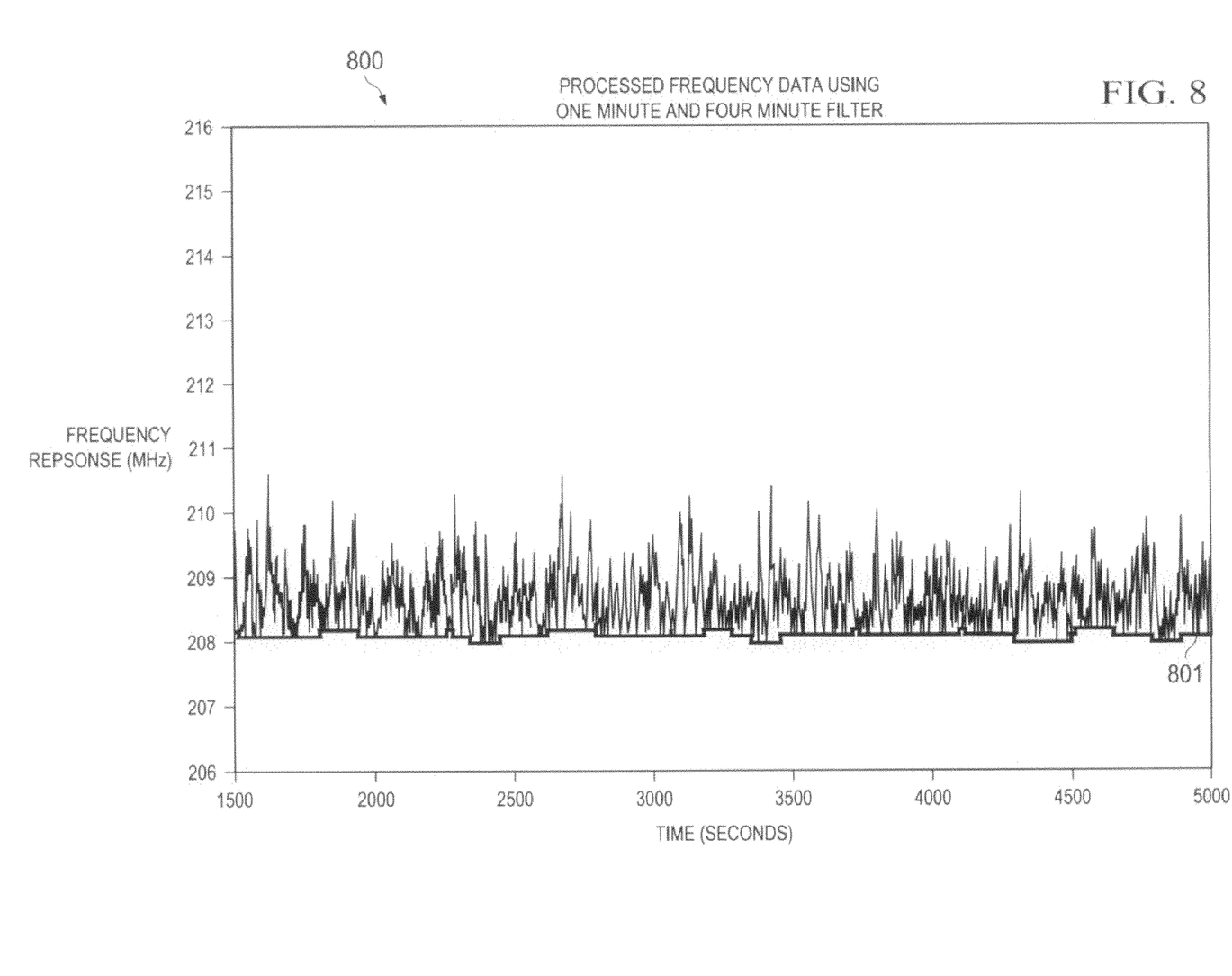
FIG. 8 illustrates a graph of frequency data filtered using a second running average filter of 24 samples (4 minutes) according to an embodiment of this disclosure.

FIG. 8 illustrates a graph 800 of frequency data filtered using a second running average filter of 24 samples (4 minutes) according to an embodiment of this disclosure. Graph 800 illustrates frequency data filtered using a second running average filter of 24 samples (4 minutes) to compensate for the gas flow pattern removal. The dark line 801 is the running average 15 minute minimum frequency that is used to derive Heuristic Salinity™.

Although the present disclosure has been described with an exemplary embodiment, various changes and modifications may be suggested to one skilled in the art. It is intended that the present disclosure encompass such changes and modifications as fall within the scope of the appended claims.

What is claimed is:

1. A system for determining a water content in a multiphase fluid flow stream, the system comprising:
    an apparatus configured to:
    obtain a series of frequency measurements of the multiphase fluid flow stream over a first predetermined time interval;
    determine a minimum frequency measurement Fmin_baseline from the series of frequency measurements;
    calculate a running average of the frequency (Fmin_gas_pattern) from the series of frequency measurements indicative of a change in a gas flow pattern of the multiphase fluid flow stream over a second predetermined time interval; and
    calculate a corrected frequency measurement F_calc_WC for determining the water content in the multiphase fluid flow stream by subtracting the running average of the frequency Fmin_gas_pattern from the minimum frequency measurement Fmin_baseline.

2. A system in accordance with claim 1 wherein the apparatus further is configured to calculate a running average F_average(t) at time t from the series of frequency measurements indicative of a water continuous phase of the multiphase fluid flow stream plus gas effects over a third predetermined time interval.

3. A system in accordance with claim 2 wherein the running average F_average(t) at time t is calculated using an frequency measurement at time t of the series of frequency measurements and a pre-determined number of frequency measurements immediately prior to the frequency measurement at time t.

4. A system in accordance with claim 2 wherein the corrected frequency measurement F_calc_WC is calculated using the running average F_average(t), and the running average Fmin_gas_pattern.

5. A system in accordance with claim 2 wherein the corrected frequency measurement F_calc_WC is calculated as follows:

$$F\_calc\_WC = F\text{min\_baseline} + (F\_average(t) - F\text{min\_gas\_pattern}).$$

6. A system in accordance with claim 1 wherein the apparatus further is configured to calculate the water content in the multiphase fluid flow stream using F_calc_WC.

7. A system in accordance with claim 1 wherein at least one of the first predetermined time interval, the second predetermined time interval, and the third predetermined time interval are selected using one or more probability density functions.

8. A method for determining a water content in a multiphase fluid flow stream using a water content measurement apparatus, the method comprising:
    obtaining a series of frequency measurements of the multiphase fluid flow stream over a first predetermined time interval;
    determining a minimum frequency measurement Fmin_baseline from the series of frequency measurements;
    calculating a running average of the frequency (Fmin_gas_pattern) from the series of frequency measurements indicative of a change in a gas flow pattern of the multiphase fluid flow stream over a second predetermined time interval; and calculating a corrected frequency measurement F_calc_WC for determining the water content in the multiphase fluid flow stream by subtracting the running average of the frequency (Fmin_gas_pattern) from the minimum frequency measurement Fmin_baseline.

9. A method in accordance with claim 8 further comprising:

calculating the water content in the multiphase fluid flow stream using F_calc_WC.

10. A method in accordance with claim 8 further comprising:

calculating a running average F_average(t) at time t from the series of frequency measurements indicative of a water continuous phase of the multiphase fluid flow stream plus gas effects over a third predetermined time interval.

11. A method in accordance with claim 10 wherein the running average F_average(t) at time t is calculated using an frequency measurement at time t of the series of frequency measurements and a pre-determined number of frequency measurements immediately prior to the frequency measurement at time t.

12. A method in accordance with claim 10 wherein the corrected electrical frequency F_calc_WC is calculated using the running average F_average(t), and the running average Fmin_gas_pattern.

13. A method in accordance with claim 10 wherein the corrected frequency measurement F_calc_WC is calculated as follows:

$$F\_calc\_WC = F\text{min\_baseline} + (F\_average(t) - F\text{min\_gas\_pattern}).$$

14. A method in accordance with claim 8 wherein at least one of the first predetermined time interval, the second predetermined time interval, and the third predetermined time interval are selected using one or more probability density functions.

15. An apparatus for measuring a water content in a multiphase fluid flow stream, the apparatus comprising:

a measurement section configured to:

obtain a series of frequency measurements of the multiphase fluid flow stream over a first predetermined time interval;

determine a minimum frequency measurement Fmin_baseline from the series of frequency measurements;

calculate a running average of the frequency (Fmin_gas_pattern) from the series of frequency measurements indicative of a change in a gas flow pattern of the multiphase fluid flow stream over a second predetermined time interval; and calculate a corrected frequency measurement F_calc_WC for determining the water content in the multiphase fluid flow stream by subtracting the running average of the frequency (Fmin_gas_pattern) from the minimum frequency measurement Fmin_baseline.

16. An apparatus in accordance with claim 15 wherein the measurement section further is configured to calculate the water content in the multiphase fluid flow stream using F_calc_WC.

17. An apparatus in accordance with claim 15 wherein at least one of the first predetermined time interval, the second predetermined time interval, and the third predetermined time interval are selected using one or more probability density functions.

18. An apparatus in accordance with claim 15 wherein the measurement section further is configured to calculate a running average F_average(t) at time t from the series of frequency measurements indicative of a water continuous phase of the multiphase fluid flow stream plus gas effects over a third predetermined time interval.

19. An apparatus in accordance with claim 18 wherein the running average F_average(t) at time t is calculated using an frequency measurement at time t of the series of frequency measurements and a pre-determined number of frequency measurements immediately prior to the frequency measurement at time t.

20. An apparatus in accordance with claim 18 wherein the corrected frequency measurement F_calc_WC is calculated using the running average F_average(t), and the running average Fmin_gas_pattern.

21. An apparatus in accordance with claim 18 wherein the corrected frequency measurement F_calc_WC is calculated as follows:

$$F\_calc\_WC = F\text{min\_baseline} + (F\_average(t) - F\text{min\_gas\_pattern}).$$

* * * * *